US00PP08697P

United States Patent [19]

de Jong

[11] Patent Number: Plant 8,697

[45] Date of Patent: Apr. 19, 1994

[54] ALSTROEMERIA PLANT MONACO

[75] Inventor: Cornelis T. J. de Jong, Roelofarendsveen, Netherlands

[73] Assignee: Agroplant-Select B.V., De Kwakel, Netherlands

[21] Appl. No.: 36,654

[22] Filed: Mar. 24, 1993

[30] Foreign Application Priority Data

Aug. 21, 1992 [NL] Netherlands ..... 12073

[51] Int. Cl.[5] ..... A01H 5/00

[52] U.S. Cl. ..... Plt./87.1

[58] Field of Search ..... Plt. 87.1

*Primary Examiner*—James R. Feyrer

[57] ABSTRACT

A new and distinct cultivar of Alstroemeria plant named Monaco, characterized by its distinctive red purple with darker reddish-purple areas outer petals, and distinguished by the off-white, yellow, and purple coloring with dark purple streaking which increase in length and width from the attachment point of the two top inner petals.

1 Drawing Sheet

BACKGROUND OF THE INVENTION

The present invention comprises a new and distinct cultivar of Alstroemeria plant referred to by the cultivar name Monaco. Monaco was originated from a hybridization program in Roelofarendsveen, The Netherlands in 1985. The female parent was cultivar number 40, an unnamed cultivar of our own selection. The male parent was No. 0 pink, a hybrid derived from own breeding. Each of the parent plants were proprietary, and have not been released or marketed, and are maintained strictly for use in the breeding program. Monaco was discovered and selected as one flowering plant within the progeny of the stated parentage by me on Jul. 12, 1985 in a controlled environment in Roelofarendsveen, The Netherlands. The first asexual reproduction of Monaco was accomplished when vegative cuttings were taken from initial selection on Nov. 6, 1985 in a controlled environment in Roelofarendsveen in The Netherlands. Horticultural examination of selected units initiated in November 1985 has demonstrated that the combination of characteristics as herein disclosed for Monaco are firmly fixed and retained through generations of asexual reproduction. The following observations, measurements and comparisons describe plants grown in Roelofarendsveen, The Netherlands under greenhouse conditions which approximate those generally used in commercial practice. The following traits have been repeatedly observed and are determined to be basic characteristics of Monaco, which in combination distinguish this Alstroemeria from its parents and all other varieties of which I am aware:

1. The outer petals have a distinctive red purple color with darker red-purple areas in the center of the outer petal body.
2. The inside portion of the two top inner petals is off-white, has a yellow spot in the center, and the most upper portion is purple similar to the color in the outer petals.
3. Dark purple streaks of increasing length and width with increasing distance from the attachment point of the two top inner petals.

BRIEF DESCRIPTION OF THE FIGURE OF THE DRAWING

The accompanying photographic drawing of a close-up of the flower in bloom and buds shows typical inflorescence and foliage characteristics of Monaco nearly as true as possible with illustrations of this type. In the following description, color references are made to The Royal Horticultural Society Color Chart (RHS). The color values were determined in the afternoon in May 1988 under natural light conditions at Roelofarendsveen, The Netherlands.

BOTANICAL DESCRIPTION OF THE PLANT

Botanical: Alstroemeria cv Monaco.

Commercial: Alstroemeria.

PLANT

A. General appearance:

*Form.*—Typical of genus, of low to very low height, upright bush forming, spreading by rhizomes.

*Height.*—Measured from the surface of the soil to the highest flowers. Height of plant varies with season and cultural conditions: Summer: about 65–70 cm. Winter: about 85–95 cm. (Height outdoors is approximately 25–30 cm during the summer and 40–45 cm during the winter).

*Quality.*—High; thick stems.

*Growth.*—Upright bush forming, spreading by rhizomes; vigor is average.

B. Foliage:

*Quantity.*—Abundant.

*Number.*—Varying from season to season through the year.

*Size of leaf.*—Length: Very short, about 7.25 cm. Width: Narrow, about 2.5 cm.

*Shape of leaf.*—Elliptical.

*Color of leaf.*—Typical for genus. Upper side: dark green. Under side: green.

*Texture.*—Smooth.

Rhizomes:

*Color.*—White.

*Size.*—Enlarged.

INFLORESCENCE

A. Bud:

*Form.*—Normal-thick.

*Size.*—Diameter: about 2.5 cm, just prior to opening. Length: about 5 cm.

*Receptacle.*—Broadly elliptical.

B. Flower:

*Size.*—Medium. Diameter: about 5 cm.

*Borne.*—Umbel of about 5 branches of substantially uniform length.

*Blooming habit.*—When grown under controlled conditions: continuous the year around. (If grown as a bedding plant, the plant would bloom freely).

*Shape.*—Cupped.

*Color.*—Outer petals: Shape: lobed. Color: Near to RHS 64-D. Lighter towards base near to 65-B, darker towards upper portion near to RHS 64D-C. Blushes in center of the body near to RHS 60-D. Reverse side: same as upper surface. Margins: very finely dentate. Inner petals: Shape: lanceolate. Color: upper petals: Body near to RHS 155-D with yellow spot near to RHS 5-C in center, towards upper portion near to RHS 64C-D; dark purple streaks that increase in length with increasing distance from the attachment points of the petals. Reverse side: near to 64C-D with white-yellow band. bottom petal: Body near to RHS 155-D with RHS 64C-D, with few streaks near the margins and apex of the petals. Margins: irregularly dentate.

*Peduncle.*—Color: Medium green. Length: About 10 cm.

*Fragrance.*—None.

*Lasting quality.*—Approximately 14 days.

C. Reproductive organs:

*Stamens.*—Number: 6.

*Anthers.*—Color: Reddish-purple.

*Filaments.*—Color: Pink (turns brownish in later stage).

*Pistils.*—Color: Anthocyanin. Number: 1.

*Stigma.*—Color: Anthocyanin.

*Fertility.*—Good.

I claim:

1. A new and distinct cultivar of Alstroemeria named Monaco, as illustrated and described herein, characterized by its distinctive red-purple with darker reddish-purple blushes outer petals, and distinguished by the off-white, yellow, and purple coloring with dark purple streaking, which increase in length and width with increasing distance from the attachment points of the two top inner petals.

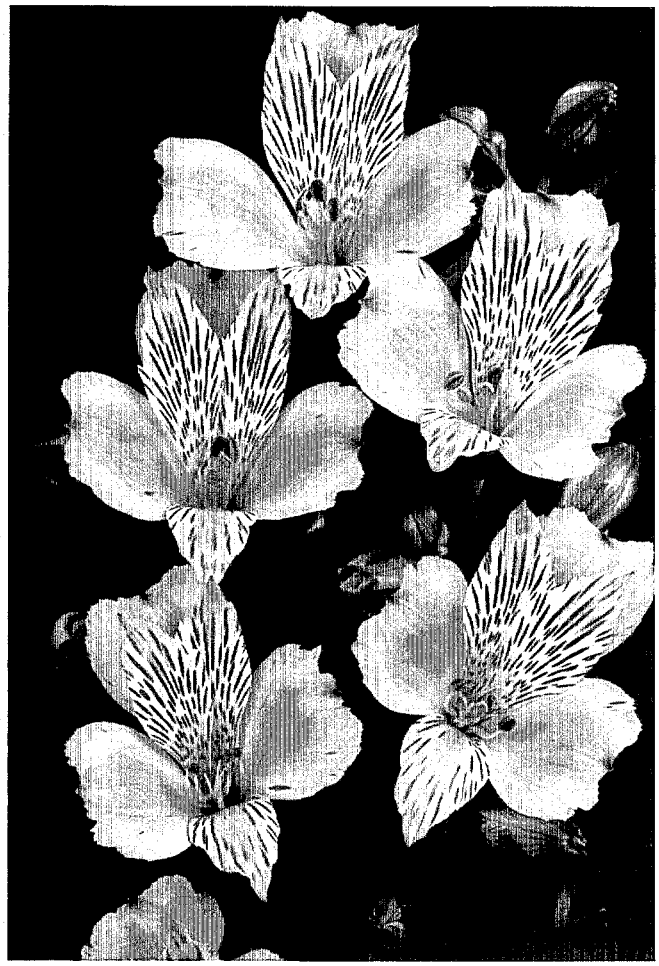

* * * * *